(12) United States Patent  
Arias et al.

(10) Patent No.: US 8,043,327 B1
(45) Date of Patent: Oct. 25, 2011

(54) AUTO RELEASE TOURNIQUET APPARATUS

(76) Inventors: Aaron Arias, Houston, TX (US); Thomas J. Brzustowicz, Houston, TX (US)

( * ) Notice: Subject to any disclaimer, the term of this patent is extended or adjusted under 35 U.S.C. 154(b) by 1028 days.

(21) Appl. No.: 11/932,973

(22) Filed: Oct. 31, 2007

(51) Int. Cl.
*A61B 17/00* (2006.01)

(52) U.S. Cl. ....... 606/203; 606/201; 24/163 R; 600/499; 128/876

(58) Field of Classification Search .............. 606/201, 606/203; 600/409; 128/876
See application file for complete search history.

(56) References Cited

U.S. PATENT DOCUMENTS

| | | | | |
|---|---|---|---|---|
| 3,587,585 A | * | 6/1971 | Ceravolo | 606/203 |
| 4,102,343 A | * | 7/1978 | Schneider | 606/203 |
| 4,125,115 A | * | 11/1978 | Mayo et al. | 606/203 |
| 6,565,592 B2 | * | 5/2003 | Mach | 606/202 |
| 2007/0173886 A1 | * | 7/2007 | Rousso et al. | 606/203 |

* cited by examiner

*Primary Examiner* — Gary Jackson
*Assistant Examiner* — Kevin Everage
(74) *Attorney, Agent, or Firm* — Egbert Law Offices PLLC

(57) ABSTRACT

An auto-release tourniquet apparatus has a strap, a housing having a first slot therein suitable for receiving a first end of the strap and a second slot suitable for receiving another portion of the strap therein, and a strap releasing mechanism positioned in the housing. The strap releasing mechanism serves to release at least one of the first and second ends of the strap from the housing after a predetermined period of time. A solenoid is positioned in the housing and acts upon the first end of the strap so as to allow for the ejection of the first end of the strap from the first slot after the predetermined period of time. A strap tensioning mechanism is associated with the second slot of the housing for allowing the strap to be suitably tensioned.

9 Claims, 4 Drawing Sheets

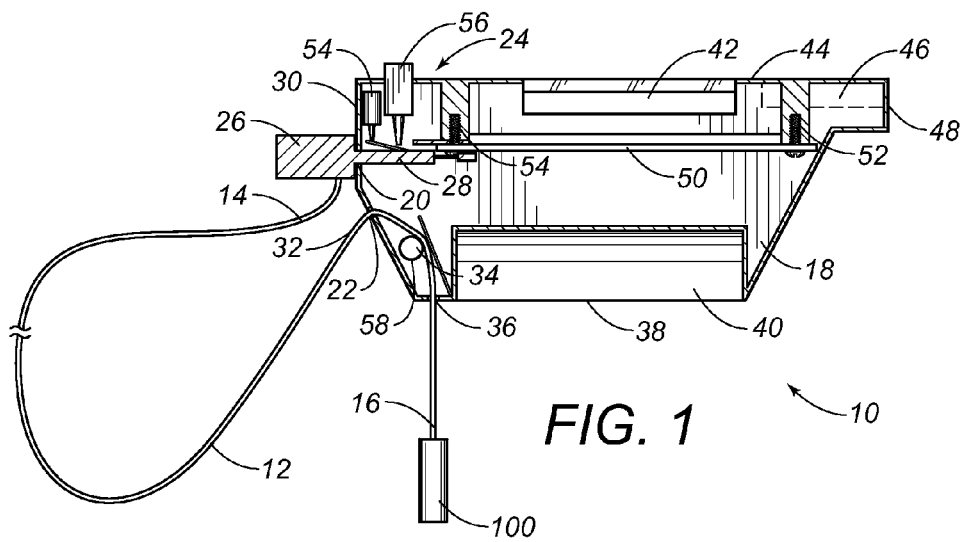
FIG. 1
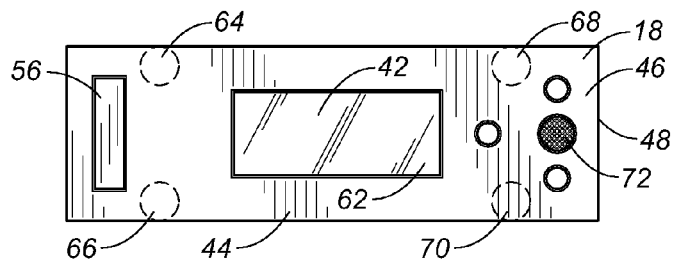
FIG. 2
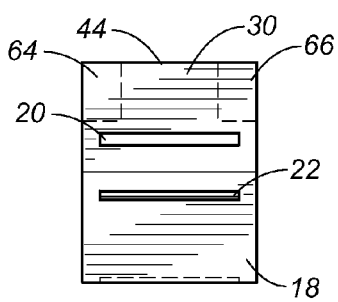
FIG. 3
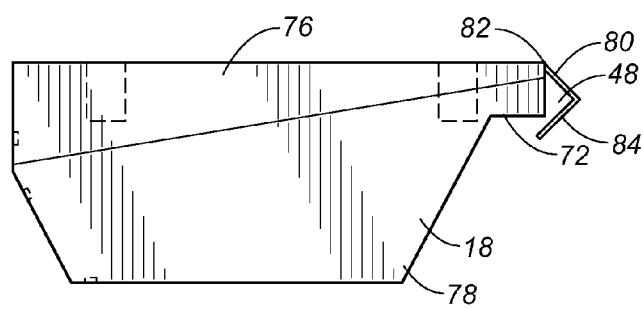
FIG. 4
FIG. 5

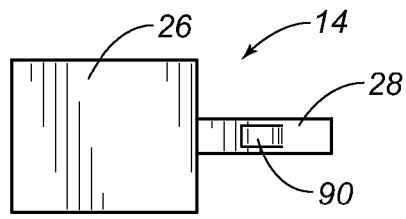
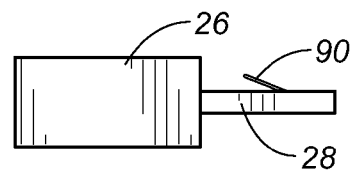
FIG. 6  FIG. 7
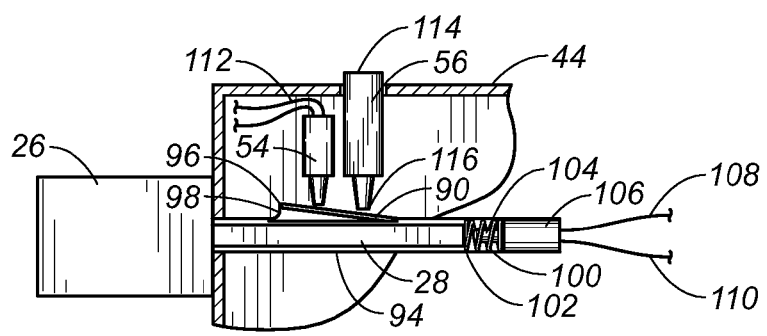
FIG. 8
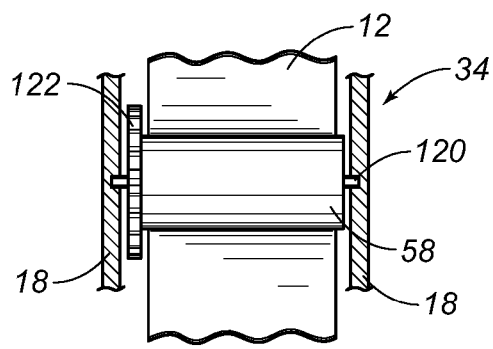
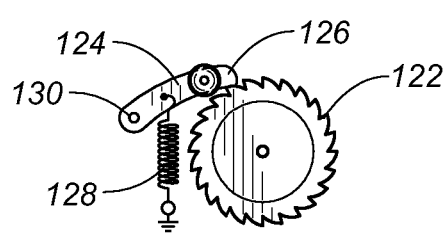
FIG. 9  FIG. 10

AUTO RELEASE TOURNIQUET APPARATUS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to tourniquets as used on a limb of a patient. More particularly, the present invention the relates to those tourniquets that are used for the drawing of blood from the patient's limb. More particularly, the present invention relates to auto-release mechanisms for mechanically releasing the tension of the tourniquet upon the limb of the patient.

2. Description of Related Art Including Information Disclosed Under 37 CFR 1.97 and 37 CFR 1.98.

Tourniquets are commonly used throughout the medical profession. Tourniquets are typically used so as to occlude the movement of blood. Typically, during the drawing of blood from a limb of a patient, a tourniquet is applied around a portion of the limb. This facilitates the ability to utilize a syringe, needle or catheter for the removal of blood. After the blood is drawn, the tourniquet is released so that normal blood flow can return to the limb of the patient.

Unfortunately, under certain circumstances, the tourniquets are not released from the limb of the patient after a predetermined period of time. Under certain circumstances, medical personnel will neglect to release the tension on the tourniquet after drawing blood. In other circumstances, the person drawing blood becomes distracted and walks away from the patient for an extended period of time. This is a particular problem where the patient is immobilized, unconscious, or unable to release the tension of the tourniquet from around the limb.

The failure to remove the tourniquet is a significant liability problem for hospitals and for medical personnel. Under certain circumstance, when the tourniquet is not removed from the limb of the patient within a predetermined period of time, there can be a significant loss of function in the limb. In other circumstances, death can occur. For example, if a tourniquet is maintained on an unconscious patient, the limb would have to be amputated before the removal of the tourniquet could occur. If the tourniquet is removed after an extended period of time, blood clots can enter the circulation system of the patient. This can often result in death, stroke or severe injury to the patient. As such, it is extremely important for the well-being of a patient that affirmative steps be taken so as to assure that the tourniquet is removed promptly each and every time that it is used.

In the past, various devices have been developed which act on pneumatic-operated tourniquets. These tourniquets are in the nature of blood pressure devices or other apparatuses. After a predetermined period of time, the air is released from the tourniquets so as to allow blood flow to be restored in a prompt manner. Various patents have issued in the past relating to such apparatuses. For example, U.S. Pat. No. 6,746,470, issued on Jun. 8, 2004 to McEwen et al., describes a pneumatic tourniquet adapted for self application by an injured person in a military or emergency situation so as to stop arterial blood loss in an injured arm or leg. This tourniquet includes a bladder having a width dimension and having a length dimension greater than the circumference of an injured limb. A clamping means is used for securing the bladder around the limb at the selected location and adapted for sealing the bladder across the bladder width to establish an inflatable portion of the bladder. This inflatable portion of the bladder is that portion of the bladder that encircles the injured limb at the selected location.

U.S. Pat. No. 6,605,103, issued on Aug. 12, 2003 to Hovanes et al., teaches a system and method for controlling pressure in a surgical tourniquet. A sensor is used to determine when flow past the tourniquet is occurring so that corrective action may be taken. This corrective action can be in the nature of increasing the pressure in the tourniquet or by notifying an operator of the flow past the tourniquet. An acoustic sensor can be used so as to indicate incipient blood flow. When the signals are detected, the tourniquet controller either incrementally increases the pressure in the tourniquet or signals an alarm indicative of the blood flow.

U.S. Pat. No. 6,051,016, issued on Apr. 18, 2000 to Mesaros et al., describes system and method of controlling the pressure in a surgical tourniquet. The pressure within an inflatable cuff surrounding a portion of a limb of a patient is changed by automatically opening a first valve connected to a controller and located in a first conduit between an inflatable bladder and the inflatable cuff when the pressure in the inflatable cuff is different from that in the inflatable bladder. Blood blow is selectively occluded within a portion of a limb of a patient within five seconds. A device is provided for detecting a leak in the tourniquet.

U.S. Pat. No. 5,842,996, issued on Dec. 1, 1998 to Gruenfeld et al., provides an automatic tourniquet system that includes a variable pressure cuff apparatus for applying a variable pressure to a limb or artery of a patient in order to occlude blood flow thereat. A control apparatus is utilized for determining the operative pressure of the variable pressure cuff. An apparatus is provided for estimating the minimum effective cuff pressure required for complete occlusion.

U.S. Pat. No. 5,181,522, issued on Jan. 26, 1994 to J. A. McEwen, shows a tourniquet system that includes an inflatable occlusive band for encircling a limb of a subject and for inflating to apply pressure to the limb in order to occlude blood flow. An inner surface of the band faces the limb. An inflation pressure regulation means responsive to a variable inflation pressure regulation signal regulates the pressure to which the occlusive band is inflated and produces an inflation pressure signal representative of the pressure to which the band is inflated. The tourniquet includes a pressure comparison means that compares the difference between the pressures represented by the inflation pressure signal and the applied pressure signal and generates an alarm signal if the difference exceeds a preassigned limit.

U.S. Pat. No. 3,095,873, issued on Jul. 2, 1963 to A. B. Edmunds Jr., shows a mechanically driven electrical recording Sphygmomanometer. In this device, a screw-type mechanism is provided along the band so as to draw the band closer together for releasing the band.

U.S. Pat. No. 2,614,565, issued on Oct. 21, 1952 to J. K. Packer, shows an automatic tourniquet which includes suitable valves for adding pressure to the limb and for releasing pressure from the limb.

U.S. Pat. No. 4,516,576, issued on May 14, 1985 to G. Kirchner, shows a tourniquet strap or band for restricting blood flow. The tourniquet includes a clamping lock and a strap which is pulled through the clamping lock and wrapped around the arm of a patient. The clamping of the strap in order to form a stanching loop occurs by means of a spring-loaded clamping wedge which clamps the strap against an inner wall of the clamping lock via a clamping plate. By manually displacing the clamping wedge against the force of the spring, the clamping force can be sensitively regulated so that a regulated release of the stanching loop is possible.

U.S. Pat. No. 5,219,356, issued on Jun. 15, 1993 to Harreld et al., provides a disposable tourniquet having an elongated, flat, stretchable band. The band has a pressure-sensitive adhesive face on one side of the band at one end and a release agent on the same face of the band but spaced from the adhesive face. The tourniquet is stored with the adhesive face folded against and adhering to the release agent. It is deployed by peeling the adhesive face away from the release agent, wrapping the tourniquet about the arm and pulling it sufficiently tight, and then adhering the adhesive face to the outside surface of the band to hold the tourniquet in place.

It is an object of the present invention to provide an auto-release tourniquet that automatically releases the tension of the tourniquet after a predetermined period of time.

It is another object of the present invention to provide an auto-release tourniquet that is portable.

It is a further object of the present invention to provide an auto-release tourniquet that is battery-operated.

It is a further object of the present invention to provide an auto-release tourniquet that displays the amount of time in which the tourniquet has been placed on the limb of the patient.

It is further object of the present invention to provide an auto-release tourniquet that sounds an alarm after an predetermined period of time.

It is still another object of the present invention to provide an auto-release tourniquet that allows for the proper tensioning of the tourniquet around the limb of the patient.

It is still further object of the present invention to provide an auto-release tourniquet that is easy to use, relatively inexpensive and easy to manufacture.

These and other objects and advantages of the present invention will become apparent from a reading of the attached specification and appended claims.

BRIEF SUMMARY OF THE INVENTION

The present invention is an auto-release tourniquet apparatus that comprises a strap having a first end and a second end, a housing having a first slot therein suitable for receiving the first end of the strap therein and a second slot suitable for receiving a portion of the strap therein, and a strap releasing means positioned in the housing. The strap releasing means is for releasing at least one of the first and second ends of the strap from the housing after a predetermined period of time.

The first end of the strap has an anchor attached thereto. This anchor has a tongue extending into the first slot. The strap releasing means acts on the tongue so as to release the first end from the housing. The first slot is a tubular member conforming to a shape of the tongue. The tubular member has an opening formed along a surface thereof. The tongue has a leaf resiliently extending outwardly of the tubular member through the opening when the tongue is positioned in the tubular member. The housing has a spring positioned therein so as to resiliently urge against an end of the tongue opposite the anchor.

The strap releasing means includes an actuating means positioned in the housing adjacent the leaf for pushing downwardly on the leaf after the predetermined period of time. The spring is suitable for ejecting the tongue from the slot after the predetermined period of time. This actuating means includes a solenoid having a arm extendable so as to push downwardly on the leaf and a controlling means cooperative with the solenoid for actuating the solenoid after the predetermined period of time. The controller is positioned in the housing and is electrically connected to the solenoid.

A button is provided having a first surface that extends outwardly of the housing and a second surface positioned adjacent the leaf. The button is depressible so as to move the leaf toward the tongue. The spring has a switching means connected hereto. The switching means serves to initiate a timer of the controlling means when the end of the tongue urges against the spring.

The auto-release tourniquet of the present invention also includes a strap tensioning means positioned adjacent the second slot of the housing. This strap tensioning means serves to apply a tension to the strap. The second end of the strap extends outwardly of the housing. The second end of the strap is pullable away from the housing so as to apply the tension to the strap. The strap tensioning means includes a roller having a surface contacting a surface of the portion of the strap, and a pinching means positioned on an opposite side of the portion of the strap from the roller. This pinching means is cooperative with the roller for applying a compressive force against respective surfaces of the portion of the strap. The roller has an axle extending centrally therethrough. A ratchet wheel is connected to the axle. A pawl is engageable with at least one tooth of the ratchet wheel. A knob is connected to the pawl and extends outwardly of the housing. The knob is movable so as to release the pawl from the tooth of the ratchet wheel. The pawl is pivotally mounted in the housing at an end opposite the tooth. A resilient member, such as a spring, is connected to the pawl between the pivotal mounting and the end adjacent the tooth so as to the pawl against the ratchet wheel. The pinching means also includes a leaf spring mounted in the housing and extending toward the surface of the portion of the strap opposite the roller.

The housing has a third slot formed therein. The second end of the strap extends through this third slot. An end cap is affixed over the second end of the strap. This end cap has a size greater than a size of the third slot.

A switching means is positioned adjacent the second slot and is cooperative with the portion of the strap. This switching means initiates a running of the predetermined period of time when the strap is tensioned. The switching means includes a switch having a button extending resiliently outwardly therefrom. The strap depresses the button so as to initiate the running of the predetermined period of time when the strap is tensioned. The switch has an end opposite the button affixed to an inner surface of the housing adjacent the second slot.

The housing has a battery compartment formed therein. A battery is received in the battery compartment. The battery is electrically connected to the strap releasing means. The anchor has a size greater than a size of the first slot. The anchor has a surface residing against a surface of the housing when the tongue is received in the first slot.

BRIEF DESCRIPTION OF THE SEVERAL VIEWS OF THE DRAWINGS

FIG. 1 is a side elevational view, in cross section, of the auto-release tourniquet apparatus of the present invention.

FIG. 2 is a plan view of the housing of the auto-release tourniquet apparatus of the present invention.

FIG. 3 is an end view of the housing of the auto-release tourniquet apparatus of the present invention.

FIG. 4 is a side elevational view of the housing of the auto-release tourniquet apparatus of the present invention.

FIG. 5 is a bottom view of the housing of the auto-release tourniquet apparatus of the present invention.

FIG. 6 is an isolated view showing the anchor and tongue at the first end of the strap of the auto-release tourniquet apparatus of the present invention.

FIG. 7 is an isolated side view of the anchor and tongue of the first end of the strap of the auto-release tourniquet apparatus of the present invention.

FIG. 8 is an isolated diagrammatic illustration, in side elevation, of the mechanism of the present invention for the release of the tongue from the tubular member of the auto-release tourniquet apparatus of the present invention.

FIG. 9 is an isolated view of the strap tensioning mechanism of the auto-release tourniquet apparatus of the present invention.

FIG. 10 is a side view of the tensioning mechanism of the auto-release tourniquet mechanism of the present invention.

DETAILED DESCRIPTION OF THE INVENTION

Figure 11:
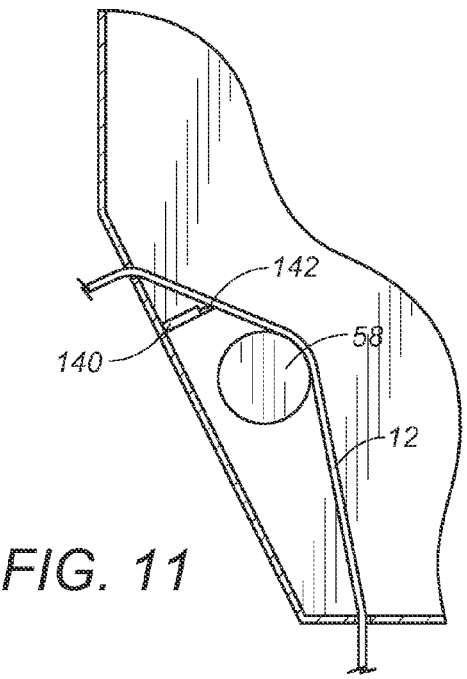
FIG. 11 illustrates the actuating of the switching system associated with the tensioning mechanism of the auto-release tourniquet apparatus of the present invention.

Referring to FIG. 1, there is shown the auto-release tourniquet apparatus 10 in accordance with the teachings of the preferred embodiment of the present invention. The auto-release tourniquet apparatus 10 of the present invention includes a strap 12 having a first end 14 and a second end 16. A housing 18 has a first slot 20 formed therein suitable for receiving the first end 14 of the strap 12. A second slot 22 is suitable for receiving a portion of the strap 12 therein. The strap 12 is illustrated as extending outwardly of the housing 18. A strap releasing mechanism 24 is positioned in the housing 18. The strap releasing mechanism 24 serves to release at one of the first end 14 or the second end 16 of the strap 12 from the housing 18 after a predetermined period of time.

In FIG. 1, it can be seen that the strap 12 is in the nature of a conventional tourniquet strap. The strap has end 14 connected to an anchor 26. A tongue 28 extends into the slot 20 from the anchor 26. As will be described hereinafter, the tongue 28 includes a small leaf spring extending upwardly therefrom. In FIG. 1, it can be seen that the anchor 26 has a surface juxtaposed against the surface 30 of the housing 18. The strap 12 extends from the anchor 26 in a circular loop. This circular loop should be of a sufficient length so as to accommodate a limb of patient therein. The strap 12 includes a portion 32 that extends into the second slot 22 and over and through a tensioning mechanism 34. The strap 12 has the second end 16 extending through a third slot 36 formed at the bottom 38 of housing 18. An end cap 100 is connected to the second end of the strap 12. End cap 100 extends outwardly of the housing 18. The end cap 100 is a plastic cap that is permanently affixed over the end of the strap 12. The end cap 100 should have a size greater than that of the third slot 36 so as to prevent the strap 12 from unraveling and passing back through the slots 36 and 22 and outwardly of the housing 18. The end cap 100 also provides a surface whereby the user can grasp the end cap 100 for the purposes of tensioning the strap 12 around the limb of a patient.

The housing 18 includes a battery compartment 40 located at a bottom thereof. A proper battery can be received within the battery compartment 40 so as to provide the necessary power to the strap releasing mechanism 24. An LCD display 42 is formed on the top side 44 of the housing 18. The LCD display 42 can provide a great deal of information to the user of the apparatus 10 including, in particular, the amount of the time that the tourniquet 12 has been applied around the limb of the patient. Various button displays and actuators 46 are provided adjacent to a side 48 of the housing 18. Also, the buttons 46 can accommodate a speaker that can provide an audible alarm, as will be described hereinafter. A printed circuit board 50 is secured in position by threaded members 52 and 54 extending into the housing 18. Circuit board 50 supports a microprocessor therein. The battery in the battery compartment 40 is electrically connected to the printed circuit board 50.

A solenoid 54 is positioned adjacent to the side 30 of the housing 18. The solenoid 54 includes an arm that is positioned proximity to the leaf spring associated with the tongue 28 of the anchor 26. A push button 56 is also positioned so as to have a portion extending outwardly of the top surface 44 of the housing 18 and a bottom surface in proximity to the leaf spring extending from the tongue 28.

The housing 18 includes the tensioning mechanism 34 therein. The tensioning mechanism 34 includes a roller 58 positioned therein and a leaf spring 60 in proximity to the roller 58. This strap 12 will have a portion extending between the leaf spring 60 and the roller 58 in the manner described hereinafter.

FIG. 2 illustrates a top view of the housing 18. As can be seen, the LCD display 42 is covered by a clear panel 62. As such, any information that can be conveyed by the LCD display 42 is protected by the clear panel cover 62. The threaded members 52 and 54 are secured to the circuit board 50 by way of posts 64, 66, 68 and 70. The various buttons 46 located at end 48 of housing 18 are provided on the top surface 44 of the housing 18. These buttons can be covered with a plastic material and sealed so as to maintain the operational condition of such buttons. A speaker 72 is provided adjacent to the side 48. Speaker 72 can provide a sound in the event of an alarm condition. The push button 56 extends outwardly above the to surface 44 of the housing 18. The button 56 has a considerable width and length so as to allow a user to easily manipulate the push button 56 so as to cause the release of the tongue 28 from the interior of the housing 18.

FIG. 3 shows an end view of the housing 18. As can be seen, the first slot 20 is located above the second slot 22. The first slot 20 will have a size that is less than the size of the anchor 26. As such, the anchor 26 can reside against the surface 30.

The anchor 26 will serve to fix the position of the tongue 28 within the interior of housing 18. Posts 64 and 66 are illustrated as extending downwardly from the top surface 44.

In FIG. 4 it an be seen that the housing 18 is formed of a top shell 76 and a bottom shell 78 that can be affixed together or molded together. A panel 80 is pivotally connected at hinge 82 at one end of the housing 18. Panel 80 has a surface 84 which will cover various mechanisms located on the bottom 86 at end 48 of the housing 18. Surface 86 can include mechanisms for recharging the battery, for data output, and for other control connections.

FIG. 5 is a bottom view of the housing 18. As can be seen, the third slot 36 opens at the bottom 18. The second slot 22 is illustrated as located away from third slot 36. The end surface 86 provides an area whereby various control mechanisms can be installed. The panel 80 can cover these control mechanisms.

FIG. 6 illustrates an isolated view of the first end 14 of the strap 12. First end 14 includes the anchor 26 and the tongue 28 extending therefrom. The leaf spring 90 is affixed to a surface of the tongue 28 and extends at an angle upwardly therefrom. The tongue 28 can have a square configuration. The anchor 26 will have a size greater than that of the first slot 20 so as to prevent the anchor 26 from entering the slot and also for the proper seating of the tongue 28.

In FIG. 7 it can be seen that the anchor 26 has the tongue 28 extending longitudinally outwardly therefrom. The leaf spring 90 extends upwardly at an angle in an uncompressed condition. When the leaf spring 90 is compressed, it will reside flat against the top surface 92 of the tongue 28.

FIG. 8 illustrates the mechanisms for the actuation of the auto-release tourniquet 10 of the present invention. In FIG. 8, it can be seen that the anchor 26 has tongue 28 extending outwardly therefrom. Tongue 28 is received within a tubular member 94 located within the housing 18. Tubular member 94 includes an opening 96 at a top surface thereof. A small lip 98 resides along this opening 96. The leaf spring 90 extends upwardly such that the end of the leaf spring 90 will slightly contact the lip 98 of tubular member 94. A spring 100 is positioned in the tubular member 94 adjacent to the end 102 of the tongue 28. A push button 104 is located interior of the coil spring 100. Push button 104 extends outwardly resiliently from switch 106. Switch 106 is connected by lines 108 and 110 to the microprocessor associated with the circuit board 50.

As can be seen in FIG. 8, the tongue 28 has been inserted into the tubular member 94. This causes the spring 100 to be depressed. It also causes the button 104 to be pushed inwardly of the switch 106 so as to actuate the switch 106. When this occurs, the timer associated with the microprocessor begins running.

In FIG. 8, it can be seen that there is the solenoid 54 that has an arm extending outwardly from a bottom thereof. The arm of the solenoid 54 is located in proximity to the leaf spring 90 associated with the tongue 28. Wires 112 provide the electrical charge to the solenoid 54.

After the predetermined period of time, a signal is sent from the microprocessor to actuate the solenoid 54. The actuation of the solenoid 54 causes the arm to move downwardly. This will push the leaf spring 90 downwardly toward the tongue 28. Once the leaf spring 90 resides against the tongue 28, the coil spring 100 will immediately eject the tongue 28 from the tubular member 94. As such, the tension on the strap 12 is immediately released. The arm of the solenoid 54 can then return to a normal position. The button 104 is then released so as to cause a stopping of the timer and a resetting of the timer for future use. When the tongue 28 is reinstalled and the button 104 is depressed, then the timer can start once again. The push button 56 provides a manual technique for the release of the tongue 28 from the tubular member 94. When the top surface 114 is pushed downwardly, the bottom surface 116 will push downwardly on the leaf spring 90 so as to cause the same action as described hereinbefore. The top surface 114 extends outwardly of the top 44 of the housing 18.

FIG. 9 is an isolated view showing the operation of the tensioning mechanism 34 of the present invention. As can be seen, the strap 12 has a portion extending across a surface of the roller 58. The roller 58 is supported upon an axle 120. One side of the axle 120 is supported by the side wall of the housing 18. The opposite end of the axle 120 is supported by an opposite side wall of the housing 18. A ratchet wheel 122 is secured over the axle 120 and against a side of the roller 58.

FIG. 10 shows the operation of the ratchet wheel 122. As can be seen, a pawl 124 has a forward end 126 that engages one of the teeth of the ratchet wheel 122. A resilient member 128, in the nature of a spring, provides a downward force to the pawl 124 so as to urge the end 126 against a surface of the ratchet wheel 122. The pawl 124 has a pivot point 130 located opposite to the end 126. The resilient member 128 is connected to the pawl 124 between the end 126 and the pivot point 130. A knob 132 extends outwardly of the pawl 124. The knob 132 can also extend outwardly of the housing 18 so as to allow the user to manually lift the pawl 124, against the force of the spring 128, so as to release the end 126 from engagement with one of the teeth of the ratchet wheel 122. As such, as force is applied to the end 16 of the strap 12, the strap 12 will be tightened over the limb of the patient. The ratchet wheel 122 serves to assure that only one direction of movement occurs. If it is desired to manually release the tension on the strap 12, then the knob 132 can be moved upwardly so that the roller 58 can rotate freely.

Figure 12:
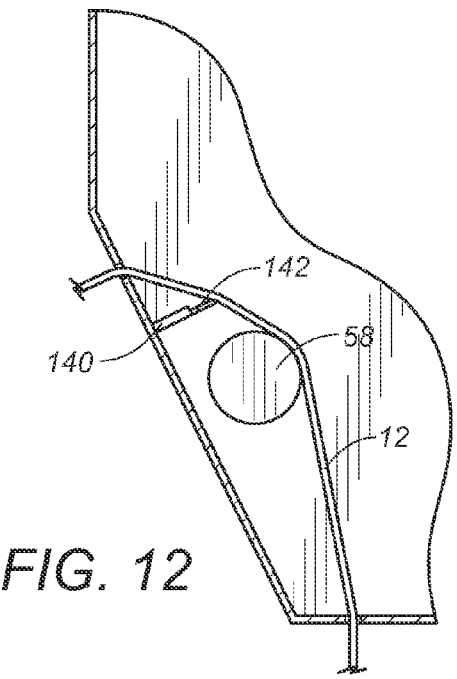
FIG. 12 shows the switching mechanism associated with the tensioning system of the auto-release tourniquet apparatus in which the switch is in a configuration and the strap is untensioned.

In FIG. 11, it is important to note that the strap 12 acts on a switching mechanism 140 located on the interior of the housing 18. In FIG. 11, the strap 12 is in its tensioned condition over roller 58. In this tensioned condition, the button 142 of the switch 140 is depressed. This can transmit a signal to the microprocessor to start the timer. The tensioning of the strap 12 provides a positive input to the microprocessor of the existence of the tension of the strap. When the tension is released, then FIG. 12 illustrates the action on the switch 140. In FIG. 12, the strap 12 is released so that it is relatively loose. As a result, the button 142 of switch 140 will push outwardly on the strap 12 since there is no tension applied thereto. Once the button 142 of switch 140 extends outwardly, the timing mechanism is stopped. The downward movement of the button 142 can restart the timer after resetting.

Referring to FIG. 12, the operation of the device is illustrated in a block diagram form. Initially, there are two ways to turn the device on. By pressing the on/off button (i.e., the button located nearest the display); and (2) by pulling the strap tight against a limb. Once the device has been turned on, it performs a quick self-test of the processor, memory, and electronics. The apparatus is then immediately ready to perform its duties. If the strap has been tightened against the limb, the device begins counting up by one-second increments of time, displaying the elapsed time on the liquid crystal display 42. At every fifteen-second interval, an audible sound is emitted by the speaker 72 as a reminder that the tourniquet is still attached and tightened on the patient's limb. When the timer counts up to its predetermined time limit, it automatically releases and rejects the removable strap anchor. This action serves to remove the occlusion.

Figure 13:
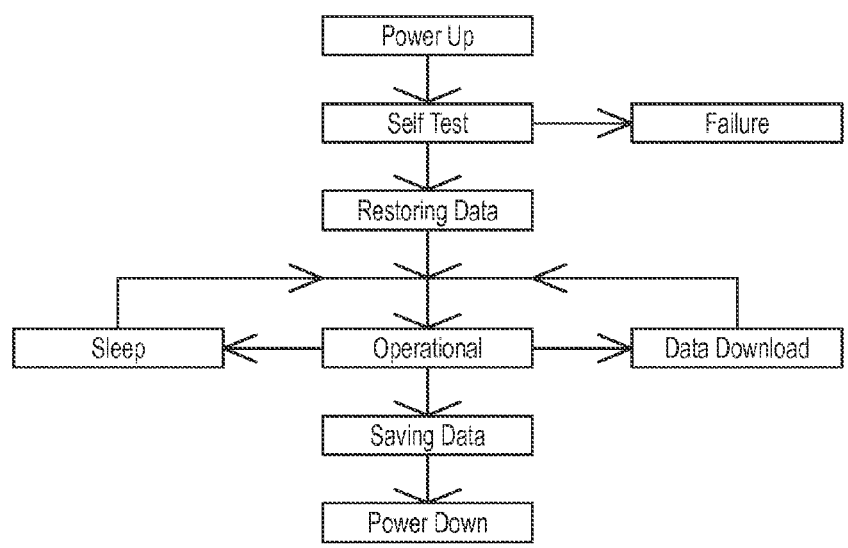
FIG. 13 is a flow diagram showing the operation of the microprocessor associated with the auto-release tourniquet apparatus of the present invention.

In FIG. 13, it can be seen that after the device has been powered up, it performs a self-test. In other words, it checks out memory and basic electronics. If a failure is detected, then the device will indicate a failure, the source of the problem and prevent further use. The data can then be restored in RAM. Once the data has been restored, the button can be pushed for a proper use. The "Data Download" is indicated by the light of an LED. If the device has been on for a period of time and nothing is done then the device moves to its "Sleep" mode. This is a low power state. When the "off" button is pressed, then data is saved and the device will "Power Down".

Figure 14:
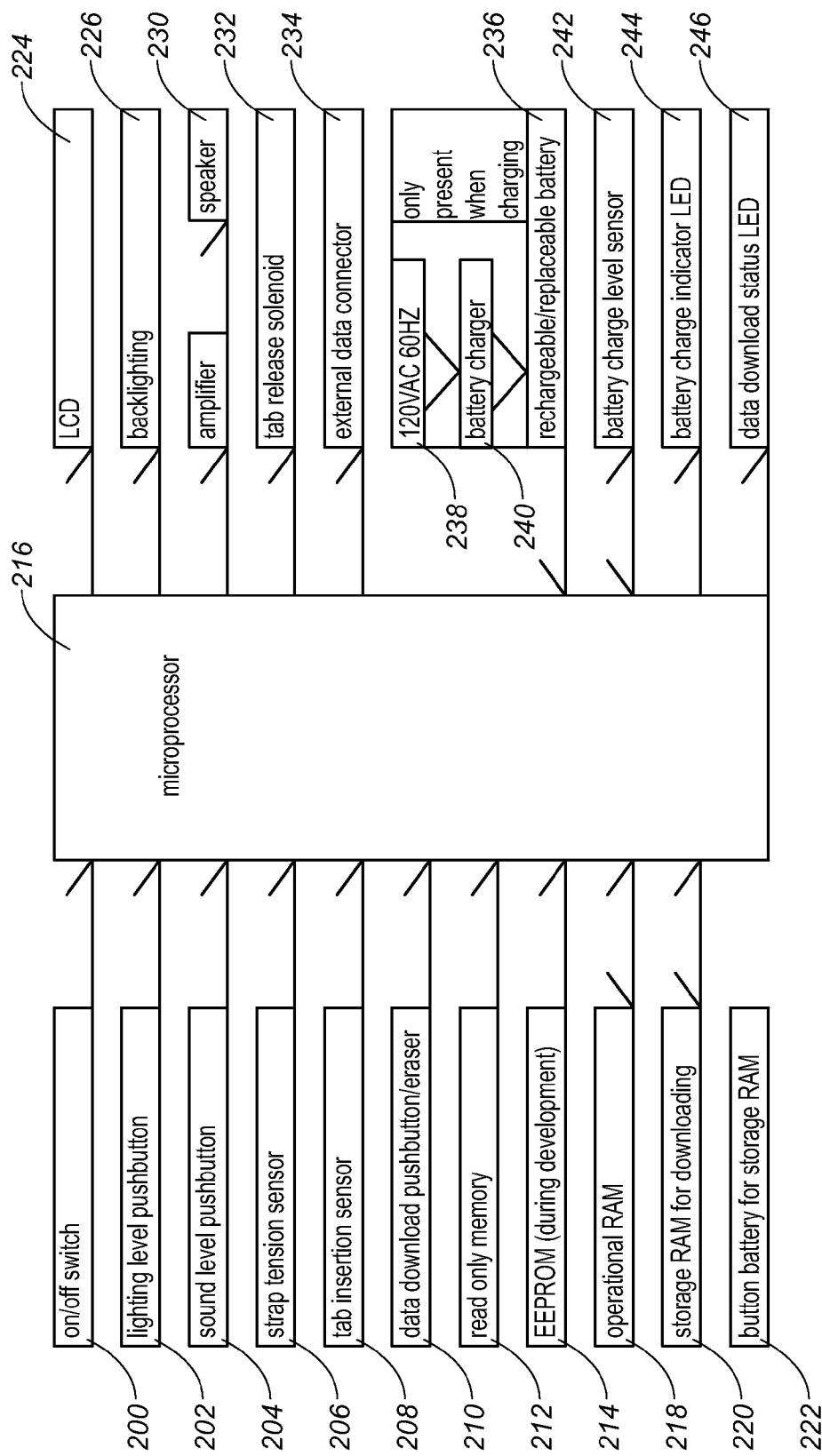
FIG. 14 is a block diagram showing the inputs and outputs of the microprocessor associated with the auto-release tourniquet apparatus of the present invention.

In FIG. 14, the operation of the microprocessor is particularly illustrated. The microprocessor receives inputs from the on/off switch 200, the lighting level push button 202, the sound level push button 204, the strap tension sensor 206, the tab insertion sensor 208, the data download push button 210, the read only memory 212 and the EEPROM 214. The microprocessor 216 interacts with the operational RAM 218 and so interacts with the storage RAM 220 for downloading. A button battery 222 provides an input to the storage RAM 220.

The microprocessor delivers an output to the LCD 224, the backlighting 226, the amplifier 228, the speaker 230, to the tab release solenoid 232, and the external data connector 234. The rechargeable/replaceable battery 236 can be charged through the use of a wall outlet 238 passing through the battery charger 240. As such, the rechargeable/replaceable battery provides a power input to the microprocessor 216. The microprocessor 216 will interact with the battery charge level sensor 242. The microprocessor 216 also delivers an output to the battery charge indicator LED 244 and to the data download status LED 246.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. An auto-release tourniquet apparatus comprising:
    a strap having a first end and a second end;
    a housing having a first slot therein suitable for receiving said first end of said strap therein and a second slot suitable for receiving a portion of said strap therein, said strap extending outwardly of said housing;
    a strap releasing means positioned in said housing, said strap releasing means for releasing at least one of said first and second ends of said strap from said housing after a predetermined period of time, said first end of said strap having an anchor attached thereto, said anchor having a tongue extending into said first slot, said strap releasing means for acting on said tongue so as to release said first end from said housing, said first slot being a tubular member conforming to a shape of said tongue, said tubular member having an opening formed along a surface thereof, said tongue having a leaf resiliently extending outwardly of said tubular member through said opening when said tongue is positioned in said tubular member, said housing having a spring positioned therein so as to resiliently urge against an end of said tongue opposite said anchor, said strap releasing means comprising:
        an actuating means positioned in said housing adjacent said leaf for pushing downwardly on said leaf after the predetermined period of time, said spring suitable for ejecting said tongue from said slot after the predetermined period of time, said actuating means comprising:
            a solenoid having a arm extendable so as to push downwardly on said leaf; and
            a controlling means cooperative with said solenoid for actuating said solenoid after the predetermined period of time, said controlling means positioned in said housing and electrically connected to said solenoid, said spring having a switching means connected thereto, said switching means for initiating a time of said controlling means when said end of said tongue urges against said spring.

2. The tourniquet apparatus of claim 1, further comprising:
    a button having a first surface extending outwardly of said housing and a second surface positioned adjacent said leaf, said button being depressible so as to move said leaf toward said tongue.

3. The tourniquet apparatus of claim 1, further comprising:
    a strap tensioning means positioned adjacent said second slot of said housing, said strap tensioning means for applying a tension to said strap.

4. The tourniquet apparatus of claim 3, said second end of said strap extending outwardly of said housing, said second end of said strap being pullable away from said housing so as to apply the tension to said strap.

5. The tourniquet apparatus of claim 4, said housing having a third slot formed therein, said second end of said strap extending through said third slot, the apparatus further comprising:
    an end cap affixed over said second end of said strap, said end cap having a size greater than a size of said third slot.

6. The tourniquet apparatus of claim 3, said strap tensioning means comprising:
    a roller having a surface contacting a surface of said portion of said strap; and
    a pinching means positioned on an opposite side of said portion of said strap from said roller, said pinching means cooperative with said roller for applying a compressive force against respective surfaces of said portion of said strap.

7. The tourniquet apparatus of claim 6, said roller having an axle extending centrally therethrough, said apparatus further comprising:
    a ratchet wheel connected to said axle;
    a pawl engageable with at least one tooth of said ratchet wheel; and
    a knob connected to said pawl and extending outwardly of said housing, said knob being movable so as to release said pawl from the tooth of said ratchet wheel.

8. The tourniquet apparatus of claim 7, said pawl being pivotally mounted in said housing at an end opposite the tooth, the apparatus further comprising:
    a resilient member connected to said pawl between the pivotal mounting and the end adjacent the tooth so as to urge said pawl against said ratchet wheel.

9. The tourniquet apparatus of claim 6, said pinching means comprising:
    a leaf spring mounted in said housing and extending toward the surface of said portion of said strap opposite said roller.

* * * * *